United States Patent [19]

Bernard et al.

[11] 4,166,077
[45] Aug. 28, 1979

[54] METHOD OF PRODUCTION OF ETHANE BY SELECTIVE HYDROGENOLYSIS OF ALKANE

[75] Inventors: Jean-René Bernard, St. Symphorien d'Ozon; Pierre Turlier, Lyons; Jacques Bousquet, Irigny, all of France

[73] Assignee: Societe Nationale Elf Aquitaine, Paris, France

[21] Appl. No.: 840,732

[22] Filed: Oct. 11, 1977

Related U.S. Application Data

[63] Continuation of Ser. No. 699,972, Jun. 25, 1976, abandoned.

[30] Foreign Application Priority Data

Jun. 30, 1975 [FR] France .............................. 75 20516
Nov. 14, 1975 [FR] France .............................. 75 34868
Dec. 16, 1975 [FR] France .............................. 75 38531

[51] Int. Cl.$^2$ .................... C07C 9/06; C10G 13/10; C07C 11/04

[52] U.S. Cl. .................... 585/310; 208/111; 208/112; 585/752; 585/905

[58] Field of Search ............... 208/111, 112; 260/676 R, 683 R

[56] References Cited

U.S. PATENT DOCUMENTS

| 3,046,317 | 7/1962 | Myers | 208/112 |
| 3,373,220 | 3/1968 | Hepp | 260/683 R |
| 3,617,511 | 11/1971 | Jenkins et al. | 208/112 |
| 3,929,619 | 12/1975 | Sinfelt et al. | 208/111 |
| 3,976,560 | 8/1976 | Erickson | 208/112 |

*Primary Examiner*—Herbert Levine
*Attorney, Agent, or Firm*—Cushman, Darby & Cushman

[57] ABSTRACT

Ethane is produced from alkanes by introducing a mixture of hydrogen and alkanes into a reactor at a spatial velocity V and a total pressure P on a catalyst at the temperature T. The catalyst is constituted by at least one metal selected from iridium and rhodium incorporated in a support of inert refractory oxide in which $SO_4^{--}$ sulphate ions are not present.

20 Claims, 3 Drawing Figures

METHOD OF PRODUCTION OF ETHANE BY SELECTIVE HYDROGENOLYSIS OF ALKANE

This is a continuation of application Ser. No. 699,972 filed June 25, 1976, now abandoned.

This invention relates to a method of production of ethane by selective hydrogenolysis of alkanes.

The reactions employed in the hydrogenation cleavage of carbon-carbon bonds are hydrocracking and hydrogenolysis. These reactions are very similar to each other but a distinction can nevertheless be drawn by considering with J.H. Sinfelt in "Advances in Catalysis" (Acad. Press. No. 23 p. 91 - 1973) that hydrocracking makes use of bifunctional catalysis, the catalyst being constituted by a cracking acid support and hydrogenating metallic sites deposited on this latter. On the other hand, hydrogenolysis makes use of monofunctional catalysis with reduced metals in which the support does not directly take part in the reaction.

From a kinetic standpoint, the reactions of the first type are of a positive order with respect to the hydrogen reagent whereas those of the second type are often of a negative order.

It can also be noted that, when catalytic acid sites are employed with a view to promoting cleavage of the carbon-carbon bonds of the hydrocarbons of the feedstock (which is the case with hydrocracking), hydrocarbons are pfreferentially formed at $C_4$ and $C_3$. This is usually what is found when examining the gas production of industrial units for catalytic cracking or hydrocracking of heavy gas-oils. Should it be desired on the contrary to promote the formation of compounds such as ethane, hydrogenolysis is undoubtedly the most favorable route.

Scientific publications relating to hydrogenolysis of paraffins are relatively numerous. Good articles which make a synthesis on this subject have been presented among others by J.H. Sinfelt (as mentioned earlier) or by J.R. Anderson in "Advances in Catalysis" (Acad. Press. No. 23 - 1973). The selectivities in general which are studied in these publications are concerned with the tendency exhibited by certain metals to demethylate the paraffins or in other words to promote scission of the carbon-carbon bonds located at one end of the chain. The selective metals for this reaction can depend on the type of hydrocarbon which is considered in the test. When $n$-heptane is employed as a test molecule the most selective metals for demethylation are palladium, rhodium and nickel (cf. J.H. Sinfelt, p. 105). On the other hand, metals such as platinum are known for their ability to effect a statistically oriented scission on all the carbon-carbon bonds of a paraffin chain.

The documentary references cited in the foregoing do not make any mention of methods which permit the achievement of selective hydrogenolysis of alkanes for producing ethane.

The aim of the present invention is to provide a method for selective hydrogenolysis of alkanes to ethane. In particular, when applied to light alkanes, the method according to the invention is conducive to the following reactions:

The catalysts employed in the method according to the present invention comprise either rhodium or iridium or a combination of these two substances or alternatively an association of one of these two metals with a metal selected from group VIII of the Periodic Table of Elements, that is to say the group comprising iron, cobalt, nickel, ruthenium, palladium, osmium and platinum, these metals being incorporated in an inert support in which $SO_4^-$ ions are not present.

The inert support is constituted by a refractory oxide which can be selected from the inert supports currently employed in heterogenous catalysis. Mention can be made by way of example of silica, the amorphous or crystallized aluminum silicates (zeolites), magnesium oxide, titanium oxide, zinc oxide and so forth.

An inert refractory oxide support is understood to mean a support which does not contain active metallic elements and does not react with the feed either by hydrogenation, isomerization, cracking, dismutation and so forth when placed in the presence of the feed under the operating conditions of the method according to the invention. Moreover, in order to ensure selectivity of the method in regard to the production of ethane, it is important to ensure that the catalyst employed has an $SO_4^-$ sulphate ion content which is as low as possible.

The $SO_4^-$ sulphate ion content will usually be less than 0.5 % by weight and preferably less than 0.1 % by weight.

The metal or metals employed are incorporated with the inert support so as to ensure dispersion within this latter; the supports employed will therefore have a large effective area.

The effective area of the inert support is within the range of 10 to 800 $m^2/g$ and preferably 50 to 500 $m^2/g$.

The catalysts in accordance with the invention have a total metal content within the range of 0.1% to 10% by weight and preferably 0.2 to 1% by weight. Furthermore, in the case in which the catalyst employed is formed by the association of two metals, one of which is iridium or rhodium and the other is another metal of group VIII, preference will be given to the choice of an atomic ratio between iridium or rhodium and the other metal of group VIII which is greater than than 0.1 and more precisely within the range of 0.16 to 8.

The metal of group VIII which is preferably employed in association with iridium or rhodium is platinum. The preferential catalysts according to the invention are thus the iridium-platinum or rhodium-platinum catalysts.

The method of selective production of ethane by hydrogenolysis of alkanes in contact with the catalysts mentioned earlier is carried out under a total pressure which varies between 1 and 80 bar, preferably between 20 and 70 bar, in order to ensure sufficient stability of the catalyst. The molar ratio at the inlet of the reactor between the hydrogen and the hydrocarbon will be maintained between 2 and 20 (preferably between 4 and 12). The temperature of reaction is closely dependent on the activity of the catalyst employed and on the pressure imposed by reason of the inhibiting effect of hydrogen on the kinetics of hydrogenolysis of alkanes. It will be possible to carry out the reaction between 150° C. and 550° C. but more usually between 300° and 450° C., depending on the type of hydrocarbon subjected to the reaction (the heaviest paraffins correspond to the lowest reaction temperatures). Another important operating variable is the hourly spatial velocity defined as the ratio of total flow rate of the reaction mixture which is assumed to be gaseous under normal conditions to volume of catalyst. The method according to the present invention is characterized by a spatial velocity within the range of 200 to 10,000 h$^{-1}$ (the low values being characteristic of low-pressure tests). In practice, that is to say at pressures at which the catalyst is stable, the spatial velocity will be within the range of 200 to 5000 h$^{-1}$.

A minimum production of at least about 39 weight percent ethane is achieved.

As can readily be understood, all that has just been explained in connection with selective hydrogenolysis of alkanes is applicable to the conversion of alkenes provided that these latter have previously been hydrogenated.

A further object of the invention is the production of ethylene from alkanes (contained for example in a light gasoline) with a very much higher yield than those which can be achieved by means of the conventional process of direct steam cracking. To this end, there will be contemplated in a first step the selective hydrogenolysis of gasoline to produce ethane and, in a second step, a reaction of steam cracking of the ethane thus formed to produce ethylene. It is of interest to note that the hydrogen produced in the second step can be employed for satisfying the hydrogen requirements of the first step. In the second step of this process, the yield of ethylene with respect to ethane can normally be expected to attain 85% by weight. If this result is then applied to those obtained by selective hydrogenolysis to ethane of the gasoline mentioned earlier, it is possible to attain an ethylene yield of 57% by weight approximately with respect to the gasoline. This result is clearly very superior to the performances which can be expected from a steam cracking operation performed in a single step on the same feedstock (25%).

Further properties and advantages of the invention will become more readily apparent from the following description of practical examples which are given by way of explanation without any implied limitation, reference being made to the accompanying drawings, wherein.

The first series of examples relates to the influence of the sulphate ions of the support on the selectivity of the bimetallic catalysts having a rhodium base.

FIRST SERIES OF EXAMPLES

A series of three catalysts containing 0.6% of rhodium and 0.4% by weight of platinum are prepared by impregnation of alumina. To this end, a certain quantity (100 g) of said alumina and a volume of solution containing on the one hand hydrated rhodium chloride RhCl$_3$, 3H$_2$O and on the other hand a platinum salt H$_2$PtCl$_6$ are brought together. The total volume of solution is chosen so as to be equal to the volume of retention of the support sample.

The solution is first placed in a beaker, the alumina is poured into the beaker in a single operation and rapid stirring is carried out until an apparently homogeneous mixture is obtained. The impregnated solid is allowed to stand for a period of 3 hours. The catalyst is then dired at 100° C. for a period of 1 hour followed by calcination for a period of 4 hours at 520° C.

The catalyst is then subjected to testing in a continuous-flow reaction vessel which operates at atmospheric pressure. First of all, the catalyst is reduced in a hydrogen atmosphere at 450° C., then tested with a spatial velocity of 500 h$^{-1}$ and a hydrogen/hydrocarbon ratio equal to 10 mole/mole. The tested hydrocarbon (alkane) is pure n-butane.

Several types of alumina have been employed for preparing the catalyst. These are all γ-aluminas which are selected on account of their low cost and availability and have closely related physical and chemical characteristics.

In this example as in the following example, the physico-chemical characteristics of the aluminas are as follows (all the percentages indicated are percentages by weight unless otherwise stated).

| Alumina | Effective area (m$^2 \cdot$ g$^{-1}$) | SiO$_2$ content (%) | Alkali-metal oxides (%) | Fe % | SO$_4^-$ % |
|---|---|---|---|---|---|
| A | 200 | 0.005 | 0.01 | 0.01 | 0.015 |
| B | 180 | 0.02 | 0.1 | 0.03 | 0.42 |
| C | 180 | 0.02 | 0.1 | 0.03 | 0.76 |

In these examples, the aluminas A, B and C therefore differ essentially in their SO$_4^-$ ion content.

The catalysts prepared respectively from the aluminas A, B and C and all containing 0.4% Pt+0.6% Rh will have the notation:

(0.4% Pt+0.6% Rh)      A (0.4% Pt+0.6% Rh)      B (0.4% Pt+0.6% Rh)      C The expression "ethane selectivity" has been adopted to designate the ratio:

$$S_{C_2} = \% \ C_2 / \% \ C_1 + \% \ C_2 + \% \ C_3$$

where % C$_i$=molar % of hydrocarbon containing $i$ carbon atoms in the hydrocarbon effluent discharged from the reactor.

By varying the temperature of the reactor, all other conditions being equal, the conversion yield (quantity of alkane converted) is caused to vary and S$_{C_2}$ is measured.

The following results are found:

| Nature of catalyst | Temperature ° C. | Conversion mole % | $S_{C_2}$ % |
|---|---|---|---|
| (0.4% Pt + 0.6% Rh) A | 150 | 18.5 | 78.5 |
|  | 170 | 81.5 | 77.5 |
|  | 190 | 99.5 | 75.6 |
| (0.4% Pt + 0.6% Rh) B | 200 | 14 | 69.5 |
|  | 220 | 37 | 69 |
|  | 240 | 92 | 67 |
| (0.4% Pt + 0.6% Rh) C | 260 | 12.5 | 55 |

-continued

| Nature of catalyst | Temperature °C. | Conversion mole % | $S_{C_2}$ % |
|---|---|---|---|
| | 370 | 41 | 28 |

This table clearly shows the harmful effct produced by the presence of the sulphate ions in the alumina both in regard to the activity of the rhodium-base bimetallic catalysts and on their selectivity.

A second series of examples shows the influence of the sulphate ions contained in the support on the selectivity and the activity of the iridium-base bimetallic catalysts.

SECOND SERIES OF EXAMPLES

A series of three catalysts containing 0.3% platinum and 0.3% iridium are prepared by impregnation of alumina. The conditions of preparation of the support are the same as in the first series of examples, the only difference being that the platinum salt employed is $H_2PtCl_6$ and the iridium salt is $H_2IrCl_6$. The aluminas A, B and C are the same as those described in the first series of examples.

The following catalysts have been tested:

| | |
|---|---|
| (0.3% Pt+0.3% Ir) | A |
| (0.3% Pt +0.3% Ir) | B |
| (0.3% Pt+0.3% Ir) | C |

The results are as follows:

| Nature of catalyst | Temperature °C. | Conversion % | $S_{C_2}$ % |
|---|---|---|---|
| (0.3% Pt + 0.3% Ir) A | 225 | 40 | 73 |
| | 247 | 85 | 75 |
| | 268 | 96 | 74 |
| (0.3% Pt + 0.3% Ir) B | 260 | 7 | 40 |
| | 300 | 38 | 65 |
| | 350 | 92 | 72 |
| (0.3% Pt + 0.3% Ir) C | (found to be inactive at any temperature below 500° C.) | | |

The third and fourth series of examples illustrate the harmful effect of the sulphate ion content of an alumina support on the selectivity of a monometallic catalyst.

THIRD SERIES OF EXAMPLES

A series of catalysts containing 0.3% by weight of iridium deposited on a high area alumina has been prepared in the laboratory by bringing together a certain quantity of this alumina (100 g) and a volume of hydrated hexachloroiridic acid solution equal to the retention volume of the support sample. The solution being placed in a beaker, the alumina is poured in a single operation and rapid stirring is effected until a homogeneous mixture is obtained. The impregnated solid is allowed to stand for a period of 3 hours; the catalyst is then dried at 100° C. for a period of 1 hour and calcined for a period of 4 hours at 520° C. The catalytic test is then carried out in a continuous-flow reactor which contains a small quantity of the catalyst and operates at atmospheric pressure.

After reducing the catalyst in a flow of hydrogen at 450° C., said catalyst is tested at a spatial velocity equal to 500 $h^{-1}$ and a hydrogen/hydrocarbon molar ratio equal to 10. The hydrocarbon employed is pure n-butane.

Several types of alumina have been employed for preparing the catalyst. These are all γ-aluminas which are selected on account of their low cost and availability; they have similar physico-chemical properties.

In this example as in the following example, the characteristics of the physico-chemical aluminas are as follows:

| Aluminas | Effective area m²/g | SiO₂ content weight % | Alkali metal oxides weight % | Iron content weight % | $SO_4^-$ ion content weight % |
|---|---|---|---|---|---|
| A' | 200 | 0.005 | 0.01 | 0.01 | 0.015 |
| B' | 325 | 0.02 | 0.7 | 0.02 | 0.09 |
| C' | 180 | 0.02 | 0.1 | 0.03 | 0.42 |
| D' | 180 | 0.02 | 0.1 | 0.03 | 0.88 |

By varying the temperature of the reactor, all other conditions being equal, the conversion yield is caused to vary and the corresponding selectivity $S_{C_2}$ is measured. The table below gives the results obtained:

| Example | Temperature T °C. | Conversion mole % | $S_{C_2}$ % |
|---|---|---|---|
| (a) Catalyst composed of 0.3% Ir on alumina A' | 192 | 20 | 78.5 |
| | 213 | 70 | 78.5 |
| | 223 | 85 | 74 |
| (b) Catalyst composed of 0.3% Ir on alumina B' | 201 | 8 | 72 |
| | 222 | 40 | 71 |
| | 242 | 83 | 69 |
| (c) Catalyst composed of 0.3% Ir on alumina C' | 322 | 6 | 58 |
| | 363 | 20 | 61 |
| | 403 | 50 | 65 |

The above table clearly shows the harmful effect of the presence of sulphate ions in alumina both in regard to selectivity and in regard to activity of the catalyst.

FOURTH SERIES OF EXAMPLES

A series of supported catalysts composed of 0.2% rhodium was prepared by a method similar to the one employed earlier (third series of examples) in the case of iridium-base catalysts. Use was made of the same alumina supports A' B' C' D' as in the previous series of examples.

The catalytic tests with pure n-butane were carried out as before and led to the results given hereunder:

| Example | Temperature T °C. | Conversion mole % | $S_{C_2}$ % |
|---|---|---|---|
| (a) Catalyst composed of 0.2% Rh on alumina A' | 170 | 47 | 68 |
| | 190 | 95 | 70 |
| | 210 | 100 | 60 |
| (b) Catalyst composed of 0.2% Rh on alumina B' | 190 | 55 | 70 |
| | 210 | 95 | 68 |
| | 230 | 100 | 56 |
| (c) Catalyst composed of 0.2% Rh on alumina C' | 210 | 17 | 65 |
| | 230 | 60 | 61 |
| | 250 | 95 | 55 |
| (d) Catalyst composed of 0.2% Rh on alumina D' | 210 | 7 | 62 |
| | 260 | 23 | 50 |

-continued

| Example | Temperature T °C. | Conversion mole % | $S_{C_2}$ % |
|---|---|---|---|
| | 320 | 34 | 34 |

To summarize, it may be stated that all the results obtained in comparison with those of the prior art make it clear that, if a monometallic or bimetallic hydrogenolysis catalyst is to be selective for the formation of ethane, it is necessary to choose a support of very high purity and especially free of sulphate ions.

It is apparent from all these results that, in order to carry out selective hydrogenolysis of n-butane to ethane, it is also possible to make use of rhodium catalysts and that these latter are better than the iridium-base catalysts.

So far as the use of rhodium is concerned and in contrast to iridium, the results of the present invention can be compared with the selectivity obtained in the case of nondispersed rhodium on a support in contact with n-butane; J.R. Anderson and B.G. Baker have in fact published the following results in Proc. Roy. Soc. Ser. A 271 p. 411 (1963):

| Temperature °K. | Conversion mole % | $S_{C_2}$ (%) |
|---|---|---|
| 368 | 100 | 18 |

A metal film of rhodium was employed and $S_{C_2}$ was calculated from the data given by the authors; these results are distinctly inferior to those found in the case of rhodium dispersed on an alumina containing less than 0.5% of sulphate ions.

FIFTH SERIES OF EXAMPLES

The object is to define the optimum composition of bimetallic compounds having an iridium base. In these examples, consideration will be given to the case of the platinum-iridium pairs supported by an alumina which is free of sulphate ions.

A series of twelve catalysts was prepared in the laboratory by the conventional method of impregnation of a pure high-area alumina (alumina A and A' of the previous examples) in the presence of an excess quantity of acqueous phase. The method employed is that which has already been described in the prior art (cf. French Pat. No. 2,080,099). This method consists in incorporating 100 g of high-purity alumina having an effective area in the vicinity of 200 m²/g⁻¹ with 100 cm³ of solution containing the desired quantities of hexachloroplatinic acid and hexachloroiridic acid with, in addition, 0.9 cm³ of a 20% solution of monoethanolamine. Prior to impregnation, steps will be taken to treat the support with 140 cm³ of water for a period of 30 minutes and, after centrifugation, with 80 cm³ of water containing 5.7 cm³ of hydrochloric acid (having a density of 1.18) for a period of 7 hours. The impregnation is more complete with gentle agitation of the solid-liquid mixture. The contacting time is 5 hours. This is followed by centrifugation, drying for a period of 1 hour at 100° C. and activation for a period of 4 hours 520° C. in the presence of air.

The twelve catalysts thus prepared correspond to the compositions given below:

| Number of catalyst | Weight % Pt | Weight % Ir | Atomic Ir/Pt |
|---|---|---|---|
| 1 | 0.28 | 0.0176 | 0.062 |
| 2 | 0.3 | 0.3 | 0.98 |
| 3 | 0.1 | 0.1 | 0.98 |
| 4 | 0.5 | 0.5 | 0.98 |
| 5 | 0.1 | 0.5 | 4.94 |
| 6 | 0.5 | 0.1 | 0.20 |
| 7 | 0.3 | 0.583 | 1.92 |
| 8 | 0.583 | 0.3 | 0.50 |
| 9 | 0.017 | 0.3 | 17.45 |
| 10 | 0.58 | 0.1 | 0.17 |
| 11 | 0.5 | 0.02 | 0.039 |
| 12 | 0.58 | 0.02 | 0.034 |

These twelve catalysts are subjected to a test consisting of hydrogenolysis of pure n-butane by pure hydrogen after preliminary reduction of the metallic phase at 450° C. for a period of 16 hours in a flow of hydrogen of 25 1/h (in respect of 3 cm³ of volume of catalyst). The reaction conditions are:

| total pressure | 1 atmosphere |
|---|---|
| spatial velocity | 500 h⁻¹ |
| molar ratio hydrogen/butane | 6 |

Under these conditions, the majority of catalysts are sufficiently stable to be capable of carrying out measurements during one day. The selectivity of catalysts is characterized by the production of ethane, consideration being accordingly given to the weight yield of ethane from n-butane (95% molar conversion). Furthermore, the activity of the catalysts will be characterized by the reactor temperature which is necessary in order to obtain a conversion of 50% (half-reaction temperature), the catalyst being more active as the temperature is lower.

Figure 1:
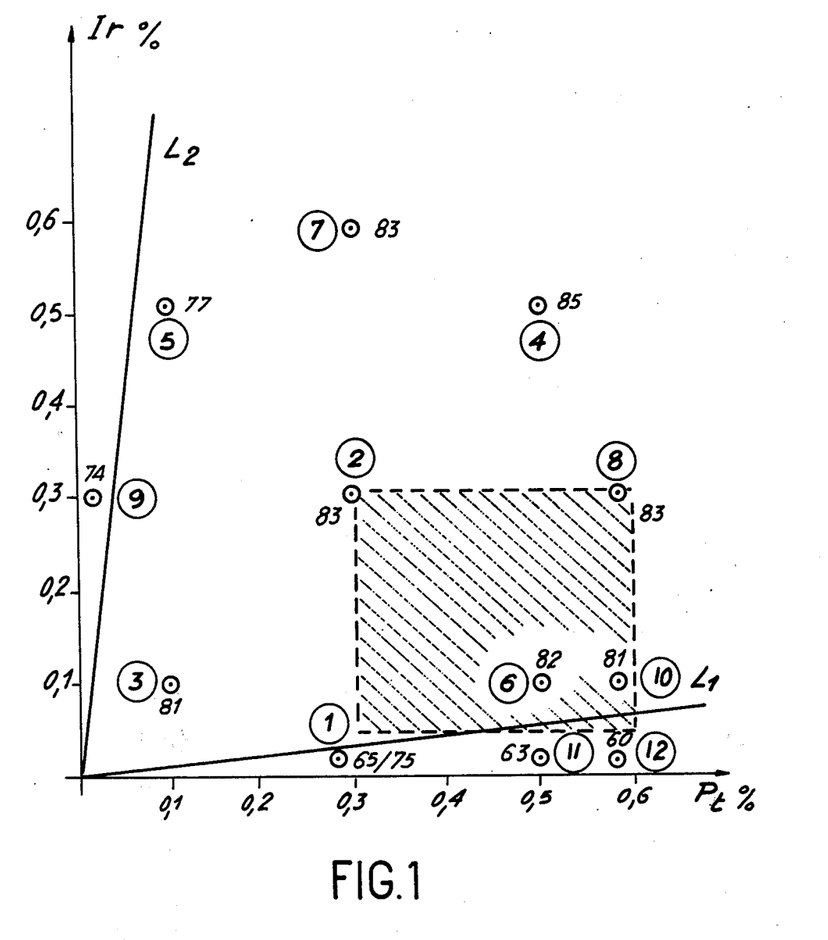
FIG. 1 shows the weight yields of conversion to ethane in respect of different values of relative concentration of the pair Pt - Ir.
Figure 2:
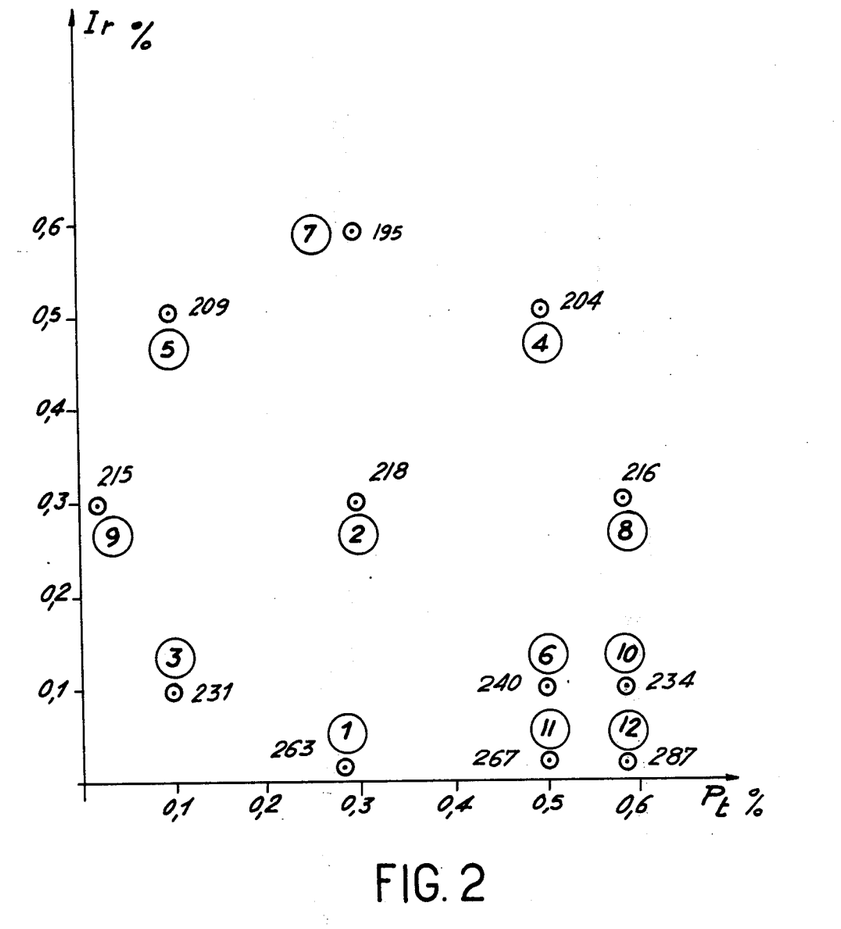
FIG. 2 shows the half-reaction temperatures in respect of different values of relative concentration of the pair Pt - Ir.

The results obtained are shown in FIGS. 1 and 2. In FIG. 1, the percentage by weight of platinum is plotted as abscissae and the percentage by weight of iridium is plotted as ordinates. There is associated with each number of the catalyst (surrounded by a circle) the number representing the weight yield of ethane. The catalysts corresponding to an atomic ratio Ir/Pt lower than 0.12 have been found to be less active, to have low selectivity and low stability. Furthermore, the catalysts corresponding to an atomic ratio Ir/Pt higher than 8 are distinctly less selective than those which have an atomic ratio Ir/Pt within the range of 0.16 to 8 (cf. FIG. 1). Thus a first preferential domain is located between the straight lines $L_1$ and $L_2$ of FIG. 1.

The temperatures of half-reaction are shown in FIG. 2 with the same coordinates as in FIG. 1. It can be seen that the activity of the catalysts increases to a slight extent with the content of iridium alone.

A further criterion of comparison of the catalysts employed in the method according to the invention is the study of the tendency of these latter to produce methane by means of parasitic reactions such as:

In the products of these reactions, methane has the disadvantage in that hydrogen cannot readily be recovered and that it cannot be utilized as a result of subsequent dehydrogenation.

Since the lowest methanizing activity has been found in the case of catalysts No 2, 6, 8 and 10, it will be considered that the best catalysts will be more especially be located within the zone (cross-hatched in FIG. 1) between these four last-mentioned formulations, that is to say in the case of a platinum content within the range of 0.3% to 0.6% and an iridium content within the range of 0.05% to 0.3%.

SIXTH SERIES OF EXAMPLES

An important parameter for the operation of the method is the hydrogen pressure, the value of which must be sufficiently high to ensure stability of the catalyst during operation of the unit. The minimum hydrogen pressure required to ensure stable operation of the catalyst depends to an appreciable extent on the nature of the feedstock to be processed. It has thus been possible to observe that, in the case of a given catalyst, the operation of the reactor with hexane is stable at 40 bar but is no longer stable at 30 bar. On the other hand, if the operation is carried out with n-butane, the catalyst is stable in the case of a total pressure of either 40 or 30 bar.

All these results are illustrated in the following table which relates to a catalyst containing 0.5% Pt and 0.1% Ir deposited on the alumina A described earlier.

|  | Nature of feedstock | | | |
| --- | --- | --- | --- | --- |
|  | n-butane | | n-hexane | |
| Pressure (bar) | 30 | 40 | 30 | 40 |
| Temperature (° C.) | 370 | 420 | 355 | 390 |
| Spatial velocity h$^{-1}$ | 1400 | 1250 | 1350 | 1350 |
| H$_2$/hydrocarbon mole/mole | 5.5 | 12 | 5 | 5 |
| Partial pressure H$_2$ (reactor inlet) (bar) | 25 | 37 | 25 | 33.5 |
| Duration of test (h) | 270 | 200 | 163 | 150 |
| Results beginning of test max. wt. % ethane in reactor-outlet gaseous effluents | 70 | 74 | 48 | 66 |
| Results end of test max. wt. % ethane in reactor-outlet gaseous effluents | 80 | 75 | 39 | 65 |
| Loss of yield recorded during period of test % | 0 | 0 | 19 | 1 |

In the case in which the catalyst is stable, the test periods indicated in the foregoing must not be considered as limiting periods. It should rather be noted that, during these test run periods, no reduction in ethane yield has been observed.

In the case in which the catalyst is stable, the operation of a selective hydrogenolysis reactor of this type will make it necessary for the operator to maintain the degree of conversion at a high level in order to maximize the production of ethane. Care should be taken, however, not to increase the temperature beyond the optimum value (420° C. and 370° C. for example in the case of n-butane in the example given in the above table). Beyond these values, reactions of hydrogenolysis of reaction products of interest are liable to appear and especially hydrogenolysis of ethane which has a very high activation energy (cf. J.R. Anderson and B.G. Baker Proc. Roy. Soc., 1963).

The part played by the pressure is clearly shown in the above table. When the pressure falls, the rate of the reaction increases considerably (reduction of approximately 50° C. in the reaction temperature between 40 and 30 bar); this is related to the well-known inhibiting effect of hydrogen on the hydrogenolysis reactions of light alkanes (cf. J.H. Sinfelt mentioned earlier).

SEVENTH SERIES OF EXAMPLES

The following table indicates the maximum ethane yields obtained in the hydrocarbon effluent by employing different charge stocks with a catalyst composed of 0.5% Pt+0.1% Ir deposited on the alumina A described earlier.

The flow rates are indicated either in hourly spatial velocity (h$^{-1}$) or in weight of hydrocarbon injected per weight of catalyst and per hour (WPH). The total pressure is 40 bar.

| Feedstock | H$_2$ hydrocarbon (mole/mole) | VVH (h$^{-1}$) | WPH (h$^{-1}$) | Temperature (° C.) | Molar conversion (%) | Weight % ethane of the hydrocarbon effluents |
| --- | --- | --- | --- | --- | --- | --- |
| n-butane | 5.9 | 1300 | 0.85 | 380 | 97.6 | 73 |
| Iso-butane | 6 | 1350 | 0.79 | 425 | 97.7 | 47 |
| n-pentane | 5.2 | 1400 | 0.88 | 390 | 100 | 62 |
| n-hexane | 5.2 | 1350 | 0.93 | 390 | 100 | 65 |
| light gasoline C$_5$ — 79° C.* | 5.5 | 1400 | 0.91 | 400 | 100 | 65 |

| *Composition of gasoline | | | | |
| --- | --- | --- | --- | --- |
| i C$_4$ | 0.01 | 2.2 D.M.B. | 0.26 3 Me Pentane | 14.1 |
| n C$_4$ | 0.25 | cyclopentane | 1.57 n-hexane | 29.4 |
| i C$_5$ | 10.1 | 2.3 D.M.B. | 1.95 Me cyclo C$_5$ | 4.6 |
| n C$_5$ | 26.0 | 2 Me Pentane | 13.8 cyclohexane | 0.9 |
|  |  |  | 2.2 D.M.P. | 0.1 |

D.M.B. = Dimethylbutane
D.M.P. = Dimethylpropane.

This example shows that isobutane has a particular behavior which is very probably related to its structure. It is in fact possible to obtain ethane from this hydrocarbon only under postulated conditions in which the catalyst is also isomerizing (which has not been observed) or in which two molecules of methane are formed with or without intermediate passing through propane. The situation is more favorable in the case of n-pentane, better in the case of n-hexane and excellent in the case of n-butane.

The light gasoline which we have tested contains high proportions of iso $C_5$ and of iso $C_6$. However, the yields obtained show that the isomer contents do not reduce the selectivity of the reaction. This difference is very marked when n- and iso-butane are compared and therefore becomes negligible in respect of $C_5$, $C_6$ and also $C_7$, $C_8$ and so forth.

EIGHTH SERIES OF EXAMPLES

All the metals of group VIII associated with iridium on a conventional inert support containing a low proportion of sulphate ions result in selective catalysts for the selective hydrogenolysis of alkanes to ethane.

The following examples relate to tests carried out at atmospheric pressure over a period of 24 hours (during which the catalyst is stable) at a spatial velocity of 500 h$^{-1}$, a hydrogen-feedstock ratio of 6 mole/mole and a feedstock consisting of pure n-butane. The catalysts are prepared by dry impregnation of a pure high-area alumina A (alumina A in the examples given earlier) in accordance with the conventional method.

In this case also, the expression "ethane selectivity" has been adopted to designate the ratio:

$$S_{C_2} = \% \ C_2 / \% \ C_1 + \% \ C_2 + \% \ C_3$$

% $C_i$ = molar percentage of hydrocarbon containing i atoms of carbon in the carbonaceous effluent.

Example a : Catalyst containing 0.3% Ir + 0.3% Pt

| Temperature (° C.) | Conversion yield (% mole) | $S_{C_2}$ (%) | % ethane (by weight) in the effluent |
|---|---|---|---|
| 225 | 40 | 73 | 30 |
| 247 | 85 | 75 | 68 |
| 268 | 96 | 73 | 79 |

Example b : Catalyst containing 0.3% Ir + 0.3% Rh

| Temperature (° C.) | Conversion yield (% mole) | $S_{C_2}$ (%) | % ethane (by weight) in the effluent |
|---|---|---|---|
| 161 | 40 | 69 | 31 |
| 181 | 89 | 70 | 65 |
| 203 | 99 | 67 | 76 |

Example c : Catalyst containing 0.3% Ir + 0.3% Fe

| Temperature (° C.) | Conversion yield (% mole) | $S_{C_2}$ (%) | % ethane (by weight) in the effluent |
|---|---|---|---|
| 210 | 15 | 71 | 11 |
| 230 | 47 | 63 | 31 |
| 250 | 93 | 65 | 68 |

Example d : Catalyst containing 0.3% Ir + 0.3% Pd

| Temperature (° C.) | Conversion yield (% mole) | $S_{C_2}$ (%) | % ethane (by weight) in the effluent |
|---|---|---|---|
| 250 | 20 | 58 | 13 |
| 270 | 56 | 64 | 39 |
| 305 | 99 | 53 | 66 |

Example e : Catalyst containing 0.3% Ir + 0.3% Co

| Temperature (° C.) | Conversion yield (% mole) | $S_{C_2}$ (%) | % ethane (by weight) in the effluent |
|---|---|---|---|
| 230 | 28 | 58 | 17 |
| 250 | 83 | 63 | 58 |
| 270 | 99.6 | 56 | 70 |

NINTH SERIES OF EXAMPLES

A series of catalysts containing rhodium to which were added the following metals:
iron
palladium
cobalt
nickel
platinum
ruthenium
iridium
was prepared by impregnation on a high-area, high-purity type A alumina of the previous examples. To this end, a certain quantity of this alumina (100 g) was placed in a volume of solution containing on the one hand hydrated rhodium chloride $RhCl_3$, $3H_2O$ and on the other hand a salt containing the addition metal. The total volume of solution is chosen so as to be equal to the volume of retention of the support sample.

The salts corresponding to the metals mentioned earlier were as follows: Fe $(NO_3)_2$; Pd $(NO_3)_2$; $PdCl_2$; Co $(NO_3)_2$; Ni $(NO_3)_2$; $PtCl_6H_2$; $RuCl_3$; $IrCl_6H_2$.

The solution is placed in a beaker, the alumina is poured in a single operation and stirred briskly until an apparently homogeneous mixture is obtained. The impregnated solid is allowed to stand for 3 hours. The catalyst is then dried at 100° C. for 1 hour, then calcined for 4 hours at 520° C.

A test is then carried out on the catalyst in a continuous-flow reactor which operates at atmospheric pressure. First of all, the catalyst is reduced in a hydrogen atmosphere at 450° C., then tested at a spatial velocity of 500 h$^{-1}$ and a hydrogen/hydrocarbon ratio equal to 10 mole/mole. The hydrocarbon (alkane) under examination is pure n-butane.

The object of the following examples is to show that the association of rhodium with other metals of group VIII makes it possible to obtain excellent selectivity for selective hydrogenolysis to ethane.

(1) Case of association of Pt-Rh

Figure 3:
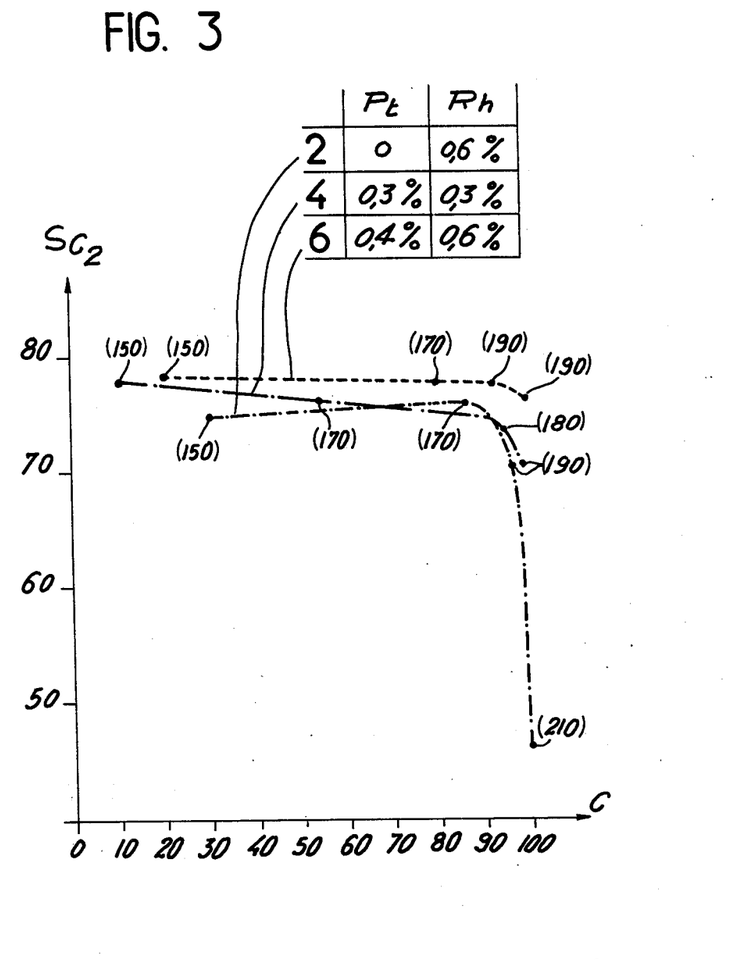
FIG. 3 shows the curves of selectivity - conversion yield - reaction temperatures which correspond to different catalysts having a rhodium base.

In FIG. 3, there is shown as a function of the conversion yield the selectivity of different catalysts which are all supported by the same alumina (A) and correspond to the following metallic compositions (the percentages indicated are percentages by weight):

Catalyst A: 0.3% Rh+0.3% Pt (curve 4)

Catalyst B: 0.6. % Rh+0.4% Pt (curve 6)

Catalyst C: 0.6% Rh (curve 2)

In FIG. 3, there is shown as a function of the molar conversion yield of n-butane the quantity $S_{C_2}$ designated as "ethane selectivity" and defined by the expression:

$$S_{C_2} = \% \ C_2 / \% \ C_1 + \% \ C_2 + \% \ C_3$$

% $C_i$ = molar percentage of hydrocarbon containing i carbon atoms in the hydrocarbon effluent discharged from the reactor.

The corresponding temperature of the reaction is indicated between brackets next to each experimental point plotted in FIG. 3. It is proved by all the results shown in this figure that, if pure supported rhodium already has appreciable selectivity as stated earlier, this latter is considerably improved when platinum is added to the rhodium and especially in the case of the catalyst which has the composition of 0.4% Pt+0.6% Rh by weight which exhibits at 190° C. a molar conversion of 99.5% and a molar selectivity of 75.7%.

(2) Case of bimetallic systems other than Pt-Rh

Bimetallic systems other than Pt-Rh have been found which are either more selective or just as selective as pure rhodium deposited on a support when the conversion rate is of high value. Thus in the case of a spatial velocity equal to 500 h$^{-1}$ and a hydrogen/hydrocarbon ratio equal to 10 mole/mole, the following results have accordingly been obtained:

| Composition of catalyst | Temperature (° C.) | Conversion C (%) | Selectivity $S_{C_2}$ (%) |
|---|---|---|---|
| 0.3% Rh | 210 | 99.5 | 58 |
| 0.3% Rh + 0.3% Pd | 210 | 99.5 | 62 |
| 0.3% Rh + 0.3% Fe | 230 | 99.5 | 60 |
| 0.3% Rh + 0.3% Ni | 210 | 99.5 | 62 |
| 0.3% Rh + 0.3% Co | 202 | 99 | 70 |
| 0.3% Rh + 0.3% Ir | 203 | 99 | 67 |
| 0.3% Rh + 0.3% Ru | 200 | 99 | 60 |

The figures given above clearly show the improvement achieved by adding metals such as Ni, Pd, Fe, Co, Ir, Ru to rhodium.

It is readily apparent that these concentration ratios are given by way of indication and are not intended to imply any limitation.

TENTH SERIES OF EXAMPLES

This tenth series consists of a detailed study of the Ni-Rh system which is prepared from a different alumina. In this case, the two metals have been incorporated in a conventional manner with the alumina support having the following characteristics: effective area of 24 m$^2$/g, alkali-metal ion content 0.08, iron content of 0.02, silica content 0.02 and sulphate content 0.01.

All the catalysts thus prepared contained 8.5×10$^{-5}$ gram-atom of total metal (Ni and Rh) per gram of catalyst. A series of catalysts having a variable rhodium content was thus prepared and tested under reaction conditions which were identical with those described earlier.

In this case the selectivity of the catalyst was characterized by the number S which is defined by the relation:

$$S = \frac{\text{relative number of moles of n-butane converted to ethane}}{\text{molar conversion percentage}}$$

The results obtained are indicated below and clearly show the synergetic effect achieved by the combination of the two metals although the effective area of the support has been considerably reduced and is located outside the preferential ranges.

| % atg Rh | S** |
|---|---|
| 0* | 0.02 |
| 20 | 0.41 |
| 40 | 0.56 |
| 60 | 0.68 |
| 80 | 0.71 |
| 100 | 0.63 |

*= corresponds to 0.5% Ni by weight in the catalyst
** = measured at the same temperature: 220° C.

ELEVENTH SERIES OF EXAMPLES

A sample of catalyst containing 0.3% by weight of Pt and 0.3% of Rh was tested under pressure for hydrogenolysis of n-butane. The catalyst proved to be stable over a period of more than 300 hours under the following conditions:

| | | |
|---|---|---|
| total pressure | : | 40 bars |
| hydrogen/nC$_4$ | : | 6 mole/mole |
| spatial velocity | : | 2700 l gas at reactor inlet/l catalyst, namely 2 kg liquid n-butane/kg catalyst. |

At 330° C., it has been possible to obtain a molar conversion rate of 95% and a percentage by weight of ethane in the gaseous effluent at the reactor outlet equal to 65% which is constant throughout the test.

At the same time, if a feed of pure n-hexane is tested under the same conditions with the same catalyst, a molar conversion rate of 95% can be obtained at 310° C. and the percentage of ethane measured in the gaseous effluent at the reactor outlet is found to be equal to 56%.

What we claim is:

1. A method of production of ethane by selective hydrogenolysis of alkanes, wherein said method comprises introducing into a reactor at a spatial velocity V a gaseous mixture of hydrogen and alkanes under a total pressure P on a monofunctional catalyst at the temperature T, and wherein said monofunctional catalyst is constituted by at least one catalytically active metal selected from iridium and rhodium incorporated in a support of inert refractory oxide essentially completely devoid of SO$_4$ ions and wherein the total percentage of catalytically active metal contained in the catalyst is within the range of 0.1% to 10% by weight thereby producing an ethane yield of at least about 39 weight percent.

2. A method according to claim 1, wherein the catalyst further comprises a second metal selected from group VIII of the Periodic Table of Elements in which said metal comprises iridium, rhodium, osmium, cobalt, palladium, iron, nickel, ruthenium and platinum and wherein the atomic ratio between the metal of the group constituted by iridium and rhodium and the other metal of group VIII is higher than 0.1.

3. A method according to claim 1, wherein the total percentage of catalytically active metal contained in the catalyst is within the range of 0.1% to 10% by weight.

4. A method according to claim 3, wherein the total percentage of catalytically active metal contained in the catalyst is within the range of 0.2% to 1%.

5. A method according to claim 1, wherein the SO$_4$ ion content of the inert support is less than 0.5% by weight.

6. A method according to claim 5, wherein the SO$_4$ ion content of the inert support is less than about 0.1% by weight.

7. A method according to claim 1, wherein the inert refractory oxide support is selected from the group consisting of alumina, silica, silicaalumina, magnesia, titanium oxide and zinc oxide.

8. A method according to claim 7, wherein the effective area of the inert support is within the range of 10 to 800 m$^2$ per gram.

9. A method according to claim 8, wherein the effective area of the inert support is within the range of 50 to 500 m$^2$ per gram.

10. A method according to claim 1, wherein the ethane so obtained is thereafter converted to ethylene by steam cracking, the hydrogen produced in the steam cracking reaction being recycled to the selective hydrogenolysis reactor.

11. A method according to claim 1, wherein the total pressure P is within the range of 1 to 80 bar.

12. A method according to claim 11, wherein the total pressure P is within the range of 20 to 70 bar.

13. A method according to claim 1, wherein the molar ratio between the hydrogen and the alkane is within the range of 2 to 20.

14. A method according to claim 13, wherein the molar ratio between the hydrogen and the alkane is within the range of 4 to 12.

15. A method according to claim 1, wherein the temperature T is within the range of 150° to 550° C.

16. A method according to claim 15, wherein the temperature T is within the range of 300° to 450° C.

17. A method according to claim 1, wherein the spatial velocity V of introduction of the hydrogen-alkane mixture into the reactor is within the range of 200 to 10,000 h$^{-1}$.

18. A method according to claim 17, wherein the spatial velocity is within the range of 200 to 5,000 h$^{-1}$.

19. A method according to claim 2, wherein the atomic ratio between the metal of the group constituted by iridium and rhodium and the other metal of group VIII is within the range of 0.16 to 8.

20. A process for producing ethane by selective hydrogenolysis of alkanes comprising:
   (1) introducing into a monofunctional catalyst-containing selective hydrogenolysis reactor a mixture of hydrogen and alkanes,
      at a spatial velocity V of 200 to 10,000 h$^{-1}$;
      at a temperature T in the range of 150° to 550° C.;
      under a total pressure P of 1 to 80 bar, said catalyst consisting essentially of at least one metal selected from the group consisting of iridium and rhodium incorporated in a support of inert refractory oxide containing less than 0.5% by weight of SO$_4$ ions, said metal being present in an amount in the range of 0.1 to 10% by weight to produce at least about 39 weight percent ethane, and thereafter
   (2) converting the ethane obtained in step (1) to ethylene, the hydrogen thus produced being recycled to the reactor of step (1).

* * * * *